(12) United States Patent
Beisang et al.

(10) Patent No.: US 8,084,513 B2
(45) Date of Patent: *Dec. 27, 2011

(54) IMPLANT FILLING MATERIAL AND METHOD

(76) Inventors: Arthur A. Beisang, White Bear Lake, MN (US); Robert A. Ersek, Austin, TX (US); Arthur A. Beisang, III, North Oaks, MN (US); Daniel J. Beisang, North Oaks, MN (US)

(*) Notice: Subject to any disclaimer, the term of this patent is extended or adjusted under 35 U.S.C. 154(b) by 160 days.

This patent is subject to a terminal disclaimer.

(21) Appl. No.: 12/463,526

(22) Filed: May 11, 2009

(65) Prior Publication Data

US 2009/0306245 A1  Dec. 10, 2009

Related U.S. Application Data

(63) Continuation-in-part of application No. 11/450,644, filed on Jun. 9, 2006, now abandoned, which is a continuation-in-part of application No. 10/839,559, filed on May 5, 2004, now abandoned.

(60) Provisional application No. 60/533,168, filed on Dec. 30, 2003.

(51) Int. Cl.
*A61F 2/12* (2006.01)
*A61K 9/00* (2006.01)
*C08L 39/06* (2006.01)
*C08L 39/04* (2006.01)
*C08L 77/02* (2006.01)

(52) U.S. Cl. ........ 523/113; 424/422; 424/484; 424/486; 623/7; 623/8; 524/548; 524/555; 525/178

(58) Field of Classification Search ................. 523/113; 424/422, 484, 486; 623/7, 8; 524/548, 555; 525/178
See application file for complete search history.

(56) References Cited

U.S. PATENT DOCUMENTS

| | | |
|---|---|---|
| 2,938,017 A | 5/1960 | Grosser |
| 3,759,880 A | 9/1973 | Hoffman et al. |
| 3,933,766 A | 1/1976 | Hofmann et al. |
| 4,731,081 A | 3/1988 | Tiffany et al. |
| 4,828,827 A | 5/1989 | Henderson et al. |
| 5,067,965 A | 11/1991 | Ersek et al. |
| 5,156,601 A | 10/1992 | Lorenz et al. |
| 5,258,028 A | 11/1993 | Ersek et al. |
| 5,258,421 A | 11/1993 | Lorenz et al. |
| 5,306,504 A | 4/1994 | Lorenz |

(Continued)

FOREIGN PATENT DOCUMENTS

WO  WO/0153359 A1  7/2001

OTHER PUBLICATIONS

Sales Specifications PLASDONE K-29/32; International Specialty Products; Aug. 4, 2008.*

(Continued)

*Primary Examiner* — Michael Pepitone
(74) *Attorney, Agent, or Firm* — Nikolai & Mersereau, P.A.; C. G. Mersereau

(57) ABSTRACT

Compositions of cross-linked polyvinylpyrrolidone (PVP) are disclosed that are generally in the form of an elastic, hydrophilic, water-insoluble viscous cohesive mass of material that has many important medical uses including uses as a filler for implants. The present invention also involves a process for producing such compositions.

19 Claims, 1 Drawing Sheet

U.S. PATENT DOCUMENTS

| | | |
|---|---|---|
| 5,480,430 A | 1/1996 | Carlisle et al. |
| 5,571,182 A | 11/1996 | Ersek et al. |
| 5,997,574 A | 12/1999 | Hayes et al. |
| 6,099,565 A | 8/2000 | Sakura, Jr. |
| 6,153,664 A | 11/2000 | Wise et al. |
| 6,410,044 B1 | 6/2002 | Chudzik et al. |
| 6,465,001 B1 | 10/2002 | Hubbell et al. |
| 6,497,729 B1 | 12/2002 | Moussy et al. |
| 6,783,546 B2 | 8/2004 | Zucherman et al. |
| 6,955,690 B1 | 10/2005 | Cao |
| 7,316,822 B2 | 1/2008 | Binette et al. |
| 2004/0018228 A1 | 1/2004 | Fischell et al. |
| 2005/0118229 A1 | 6/2005 | Boiarski |
| 2006/0228317 A1* | 10/2006 | Chrisstoffels et al. ....... 424/70.7 |

OTHER PUBLICATIONS

Search Report dated Jan. 28, 2011.

* cited by examiner

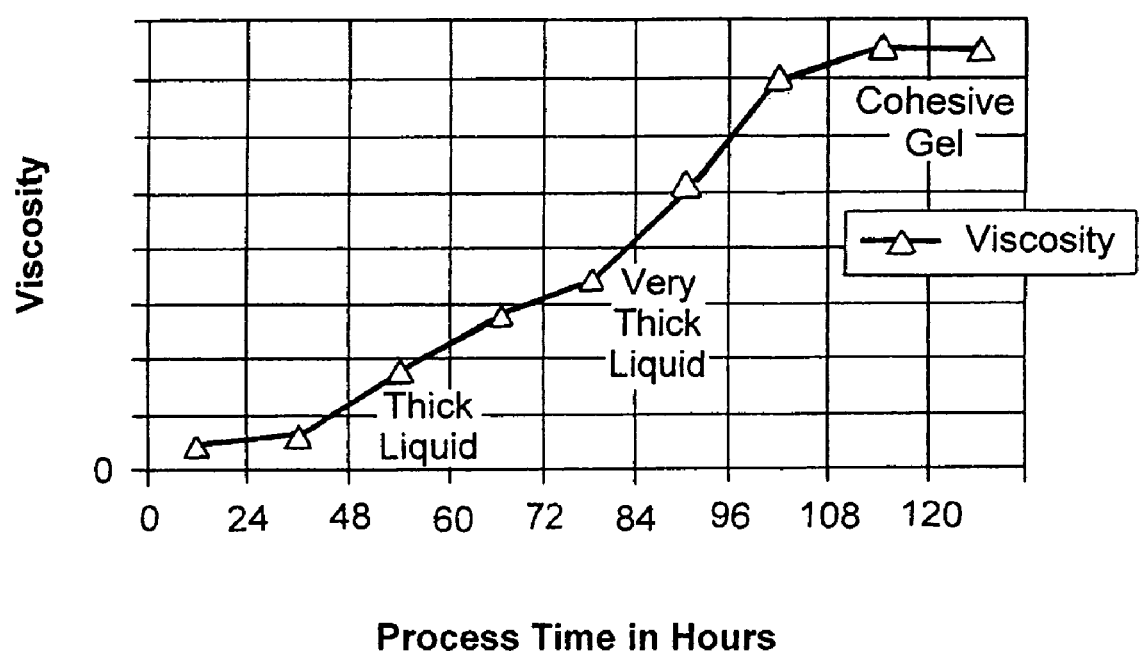

IMPLANT FILLING MATERIAL AND METHOD

CROSS-REFERENCED TO RELATED APPLICATIONS

The present application is a Continuation-In-Part of application Ser. No. 11/450,644, filed on Jun. 9, 2006, now abandoned, which, in turn, was a Continuation-In-Part of application Ser. No. 10/839,559, filed on May 5, 2004, now abandoned, the entirety, both of which, are incorporated herein by reference for any purpose. application Ser. No. 10/839,559, in turn, claimed priority based on provisional application No. 60/533,168, filed Dec. 30, 2003, which is hereby also incorporated herein by reference in its entirety.

STATEMENT REGARDING FEDERALLY SPONSORED RESEARCH OR DEVELOPMENT

Not applicable

BACKGROUND OF THE INVENTION

I. Field of the Invention

The present invention relates generally to medical implants and, more particularly, to implantable prostheses and materials used for same. The invention also relates to a process for making such materials.

II. Related Art

Medically implantable prostheses, exemplified by breast implants, are well known in the art. Such implants generally comprise a formed body presenting a nonreactive, biocompatible outer surface to surrounding tissue following implantation. Fluid-filled medical implants generally comprise a viscous fluid contained within an elastomeric shell. It has been observed that fluid-filled medical implants may leak or rupture following implantation and require explanation. The escaping fluid filler material may be contained within a periprosthetic capsule that forms around the prostheses after implantation, or it may be released into the body. It would present a desirable advantage to provide a filler for an implantable soft tissue prosthesis wherein the filler itself is substantially cohesive to facilitate removal of the filler from the body in the event of a rupture. It would present an additional advantage were this material composition nontoxic and preferably bioabsorbable.

Filling materials disclosed in previous patents relating to breast implants containing the polymer polyvinylpyrrolidone (PVP) have had some drawbacks that have been demonstrated and reported in the cosmetic plastic surgery literature. These implants generally are constructed with a silicone membrane shell. These drawbacks relate to the osmotic pressure created within the silicone shell membrane of the breast implant by the PVP solutions that have been previously utilized as filling material in clinical settings. The drawbacks also relate to control of the viscosity, cohesiveness, and elasticity of the PVP mixture used for filling breast implants.

Cross-linked PVP has a history of patented processes for the preparation of cross-linked PVP products, now commercially available from two major corporations: ISP and BASF. Three such patents are U.S. Pat. Nos. 2,938,017, 3,759,880, and 3,933,766. In the previous literature describing the process for obtaining cross-linked PVP, the temperature at which the cross-linking of PVP occurred has been required to be 100° C. or higher. Known processes for cross-linking PVP have required compounds or conditions which make them difficult to control. The rapid rate of cross-linking PVP in the aforementioned patents prohibits precise control of the cross-linked PVP products. Prior processes including that described in U.S. Pat. No. 3,933,766 call for the use of a cross-linking compound such as a cyclic acid amide or alkoxides in high pH environments (10-12 pH) or special commercial chemical "cross-linkers" at temperatures of 150° C. and pressures of 100 mm Hg.

Tacky, hydrophilic gel dressings have been disclosed using poly(N-vinyl lactam)-urethane gels in which the poly (N-vinyl lactam) may be polyvinylpyrrolidone (PVP) in U.S. Pat. Nos. 5,156,601 and 5,258,421. A skin adhesive hydrogel formed by mixing high molecular weight PVP having ring opened pyrrolidone groups and a multi-functional amine-containing polymer is disclosed in U.S. Pat. No. 5,306,504.

A further patent to Hayes et al, U.S. Pat. No. 5,997,574, discloses a medical implant which includes a shell and a filler material in which the filler material requires a combination of materials, namely, both a rheological agent and an osmotic control agent that is different from the rheological agent. In particular, Hayes et al teaches the use of polyvinylpyrrolidone (PVP) as an osmotic control agent in combination with a gum, preferably guar gum, as the rheological control agent. The combination is considered essential in order to provide a filler material having the desired properties for a breast implant, for example. The filler material of Hayes et al, further, is a one-phase, water-soluble mixture.

A long-standing need in the art for an improved formulation of PVP mixture for a filling material in breast implants has been recognized by the inventors and a new formula has been compounded and proposed. Accordingly, one aspect of the present invention relates to an improvement in cohesiveness, osmolarity, elasticity, and the viscosity of cross-linked PVP mixtures and mixtures of cross-linked PVP derivatives so that they can be controlled to be more favorable as filling material for breast implants and other uses. The proposed material composition is a viscous, highly elastic and cohesive mass comprised primarily in one embodiment of a lattice of water-insoluble, heat-treated, cross-linked PVP and water.

SUMMARY OF THE INVENTION

According to the present invention, there is provided a composition of cross-linked PVP that is in the form of an elastic, hydrophilic, water-insoluble viscous cohesive mass of material that has many important medical uses. The present invention also involves a process for forming such a composition.

By way of definition, as used herein, the term "cohesive mass" refers to a unitary body composed of a pliant material, wherein when the unitary body is subjected to an external force directed toward disrupting the cohesive structural integrity of the unitary body, the unitary body resists fragmentation and retains its structural integrity.

Thus, the cohesive mass is a material consisting essentially of an aqueous solution of a single polymeric agent and a base and is preferably in the form of a hydrogel, or the like, that possesses generally gel-like elastic properties. Hydrogels, or water-containing gels, are defined as polymers characterized by hydrophilicity and insolubility in water. In water, they swell to an equilibrium volume, but preserve their shape, the hydrophilicity being due to the presence of water-solubilizing groups and the stability of the shape due to the presence of a three-dimensional network. Most preferably, the compositions of the cohesive mass of the present invention consist essentially of materials which are insoluble in water, but which are able to imbibe water to achieve a maximum, stabilized volume without loss of shape or mechanical strength.

They further do not require additional rheological agents such as gums to operate successfully as filler materials for medical implants. Thus, the filler materials of the present invention may also be said to be free of separate rheological control agents that characterize certain earlier filler materials. Smaller trace amounts of other materials may be present which do not affect the essential properties of the stable gel-like mass. Thus, the cohesive mass may be said to consist essentially of a hydrogel and may be referred to as such. Also, the composition may be referred to as cross-linked PVP and may include chemically modified PVP or PVP derivatives which result from a process of the invention.

The process of the invention involves a heat-treatment step and a single polymeric agent in which a mixture consisting essentially of a water solution of PVP and a minor amount of a basic material such as sodium bicarbonate ($NaHCO_3$) or sodium hydroxide (NaOH), for example, are heated at a temperature preferably above about 37° C. that may be approaching, but generally remaining below the boiling point of water, preferably 90° C. to 99° C., i.e., just below 100° C., at a pressure of about 1 atm., for a sufficient time to produce the desired amount of reaction in the PVP. A temperature of 100° C. or above may be employed under certain circumstances. This results in a cross-linked or otherwise modified PVP polymer mass which can be described as cross-linked PVP or a modified PVP or a PVP derivative as the exact chemical structure is not known. The viscosity of fully processed material has been observed to be about 45,000 centipoise. One material was observed to be a 42% lattice of water-insoluble, heat-treated, cross-linked PVP and water.

In accordance with the process of the invention, it has been found that a solution containing K-30 PVP, for example, and an amount of sodium bicarbonate which is about 1% of the weight of the PVP, which is held for about 80 hours at 90°-99° C., will produce a viable cohesive mass suitable for implants closely mimicking breast or other bodily tissue. The reaction can be carried on in the actual shell of use or in a shaped vessel shell that can later be dissolved away, if desired. The process also includes steps for the removal of unwanted high molecular weight fractions of PVP prior to heat treatment. The processing temperatures of the present invention enable the heat-treated material to maintain its initial volume. This is an important factor in the manufacture of implant products.

An amount of water is added to the water-insoluble gel mass to maximize and stabilize the final volume of the gel mass. The final equilibrium or stabilized volume is reached in about 40 hours or less and requires from about 25-30% by weight of water.

The maximized, stabilized reacted mass may then be neutralized in an aqueous acid or base solution, as necessary. The strength of the acid or base solution is preferably such that the pH of the neutralized, stabilized material is close to neutral such as 7.0±0.6. Any remaining solution can be decanted off and in a well known manner. Preferred acids include HCl and NaOH is the preferred base. Alternatively aqueous HCl or NaOH solution may be used to stabilize the water-insoluble gel mass to accomplish stabilization and neutralization in a single step. In this regard, it has been discovered that the cohesive water-insoluble gel mass of the invention is extremely chemically inert and the basic characteristics of the gel produced by the process of the invention are not altered by exposure to either very strong base or very strong acids.

It has been found that various embodiments of the cross-linked PVP or PVP derivative, which makes up the cohesive mass, have a variety of additional medical uses. In this regard, for example, the material in sheet form can be utilized to prevent adhesions after surgical procedures by placing a sheet between the organs and the incision site. This property may be enhanced by removing additional water from sheets of the cohesive mass composition by heating or freeze drying. The material is also capable of being extruded through a syringe needle and injected by bolus injection as a filler for tissue or as a carrier for drugs or other therapeutic agents in treatment of human subjects.

BRIEF DESCRIPTION OF THE DRAWING

FIG. 1 represents a curve of viscosity of processed PVP material versus time as an illustration of the general process results.

DETAILED DESCRIPTION

As indicated, previous literature demonstrates that the cross-linking of PVP must take place in the presence of cross-linking agents or compounds such as cyclic acid amides; and previous literature indicates that the cross-linking of PVP must take place at temperatures of 100° C. or higher. Prior formulations of PVP incorporate between 4% and 25% by weight of PVP in water, and the swellable gels which can be formed in these processes do not have viscosities approaching even 15,000 cp. It was, therefore, unexpected that the present invention could result in a highly elastic, extremely viscous, hydrophilic, swellable, cohesive mass with controlled rates of the cross-linking or other reaction occurring at between 37° C. and 100° C. This occurs without any commercial "cross-linker" and only 0.427% by weight of biocompatible sodium bicarbonate added to the PVP-initial water solution; and the PVP-water solution is about 42% PVP by weight. The resulting product can include an insoluble PVP lattice and soluble PVP which requires filtration to separate the two phases. Centrifugation surprisingly, and unlike other processed cross-linked PVP does not separate the cross-linked PVP lattice from the soluble PVP.

When NaOH is added to water ions of sodium and hydroxide are found in solution in the water, the ions behave in a normal manner with a predictable osmotic effect and pressure. A measurement of the osmotic pressure of the ion solution can be determined with any standard freezing point depression test apparatus. When PVP is mixed with water, however, ions of PVP are not found in solution. The PVP molecules have hydrophilic sites and a mixture of PVP and water appears to be a solution of PVP. However, a freezing point depression measurement of the PVP (osmotic pressure) is not accurate or consistent.

Although water will move through a semi-permeable membrane from one side with pure water to another side of the membrane containing a PVP water mixture, the force driving the water through the membrane does not behave according to the osmotic pressure calculation calculated from the PVP concentration. The inventors have discovered that the force that drives the water is the hydrophilic attraction of sites along the PVP molecule that become hydrated. Therefore, the amount of water that will be drawn through a semi-permeable membrane is directly related to the number of hydrophilic sites on the total weight of PVP that can be hydrated.

The inventors have discovered that conditions can be created wherein PVP molecules of a specific molecular weight and concentration in a water mixture can link, coil, kink and compress into a water-insoluble, cohesive, flexible, biocompatible gel mass. The cohesive gel mass will increase in volume to a stable volume when all of the available hydrophilic sites on the PVP molecule have become saturated with water.

The weight of water which is absorbed into the cohesive water-insoluble gel mass to bring it to a final, stable volume is always equal to about 25% to 30% of the initial cohesive, water-insoluble gel mass.

It has further been discovered that the volume of the material can be stabilized to a maximum and final volume so that the filling material in a prosthesis, or the like, is stable and predetermined. It is also important that the final pH of the implant filling material can be adjusted while a stable final volume is maintained.

Accordingly, the cohesive mass of intermediate material is preferably further processed to form the final gel or cohesive mass in accordance with the invention. This involves a stabilizing step in which the gel formed in the previous step is exposed to an amount of water which, when absorbed by the gel material, swells the gel material while, at the same time, stabilizing the gel to a maximum or equilibrium volume with respect to its hydrophilic nature. Thus, in this step, the gel is seen to swell a certain amount as it takes on water by absorption until its hydrophilic nature is satisfied and it becomes stabilized in volume. The volume-stabilizing aspect is important for many uses of the gel material inasmuch as swelling of the gel as it takes on additional water in certain implanted uses is highly undesirable. Thus, the establishment of volume stability prior to final use may be quite important.

As indicated above, a neutralization step may be utilized separately or as part of the hydrolyzing/stabilizing step mentioned above. Depending on the pH acquired by the insoluble gel mass, an acidic or basic solution may be utilized to neutralize the water-insoluble gel mass. Preferentially, the resulting product should have a pH of about 7.0±0.6. If the gel produced by the product of the present invention, for example, is found to be basic in nature, it has been found that a solution of hydrochloric acid (HCl) can most conveniently be used to neutralize the product. A solution of HCl having a pH of 1.0 or less has been used to neutralize the material.

The above formulation for the cross-linked PVP mixture of the present invention has been physically mixed and compounded and measurements of essential physical characteristics such as viscosity, pH, weight, and freezing point depression of the invented mixture have been recorded. Implants containing the new formulation of cross-linked PVP were found to be stable after being treated and tested by placing them in a normal saline bath at body temperature (37° C.), and at 1½ times body temperature (55° C.) and at room temperature (25° C.) for a period of sixteen months. The new formulation was designed to improve the viscosity, cohesiveness, elasticity, and eliminate any problem that might occur from hypertonic formulations that had been previously recorded in the literature as increasing the volume and weight of implanted breast implants. For example "Long Term Results of MISTI Gold Breast Implants: A Retrospective Study", Hildegunde Piza-katzer, MD., et. al., Plastic and Reconstructive Surgery, November 2002. The formula of the present invention has resulted in forming a highly viscous very cohesive and elastic mass of cross-linked PVP when treated for the appropriate length of time (see FIG. 1) at a temperature generally not exceeding that of boiling water (100° C.). The data for the graph of FIG. 1, for example, was acquired at a reaction temperature of 95° C.

In conjunction with the present invention, it should be noted that the precise chemical reactions that occur during the processing of the PVP in accordance with the process of the present invention are somewhat unclear. As far as it is presently understood, it is believed that the PVP polymer undergoes chemical changes during the heat treating step. These changes are believed to involve opening of the lactam ring that is part of the original PVP polymer, resulting in the formation of amino acid groups that are incorporated into the "modified" polymer. Thus, in this case, of course, the heat-treated polymer may no longer be a simple PVP structure. It may be a PVP that has been modified to create new chemical moieties incorporated into the polymer structure. Such modifications may likely be responsible for the ability of the material to possess its gel-like properties. This being the case, as indicated, references to cross-linked PVP herein, with respect to the materials produced by the present process are meant to include such modifications of PVP or derivatives of PVP as might occur as a result of the process of the invention.

According to an important aspect of the present invention, it has been found that a water mixture of PVP and sodium bicarbonate can be maintained at a constant volume and weight when it is heated at a temperature between normal body temperature and the boiling point of water so that the material will maintain its original volume and weight for as long as water is not lost from the system. The temperature at which the mixture is heated along with the length of time the mixture is heated at a given temperature precisely results in a viscosity that is controlled to be anywhere between the viscosity of the beginning mixture (approximately 1000 cp) to viscosity of the cross-linked PVP viscous cohesive mass (about 45,000 cp) (see FIG. 1). It has been determined that the viscosity of the initial formulation can be increased in a controllable manner by the treatment of heat over a period of time. The volume of the initial mixture is held constant in a controllable manner. The cohesiveness is increased in a controllable manner, and the osmotic pressure is eventually made irrelevant as the heat treatment viscosity and temperature is increased in a controlled manner.

It has been demonstrated, for example, that a viscosity greater than 15,000 centipoise and up to about 45,000 centipoise maximum cohesiveness and elasticity of the cross-linked PVP cohesive mass is achieved with no change in volume or weight of the mixture. It appears that the osmolarity is almost irrelevant at this level of viscosity and cohesiveness because the cross-linked insoluble PVP cohesive mass does not appear to have a significant osmotic pressure. Thus, the composition has essentially all of the PVP cross-linked or otherwise entrapped in the viscous cohesive mass structure which results in low or no osmotic pressure. In addition, PVP is hydrophilic; therefore the hydrophilic force may work to prevent water from moving out of the breast implant through the silicone membrane to dilute the higher osmotic pressure of the tissue fluids. This of course is a very significant factor and a great improvement in PVP filling materials for breast implants.

The formulation of water, sodium bicarbonate and PVP can be treated for a period of time at a temperature below boiling necessary to achieve viscosities greater than 15,000 centipoise and up to about 45,000 centipoise form a completely cohesive, water-insoluble mass with no change in weight or volume. The cohesive mass that is formed contains substantially all of the initial water but the PVP is no longer soluble and is in the form of a viscous cohesive mass in which the insoluble PVP remains hydrophilic.

The above properties are all desirable characteristics for a breast implant filling material and such a filling material will eliminate several negative aspects of filling materials previously used. Sodium hydroxide may be substituted for sodium bicarbonate in the initial mixture with the identical PVP cross-linked hydrogel being formed. It is contemplated that other ionic molecules may also occur to those skilled in the art to be substituted for sodium bicarbonate. It will be appreciated that the general process for making the above-described cohesive mass has useful applications in various medical fields. Some of these will be described.

First Embodiment

First, PVP and sodium bicarbonate are dissolved in water in a ratio recorded hereafter. The materials must be dissolved thoroughly and the mixture degassed, if needed. The mixture is then introduced into an implant shell, such as any silicone shell for a penile implant or breast implant or any kind of an anatomical implant that can be filled with this mixture. In the next step, the implant shell is heated containing the mixture at a temperature that remains below the boiling point of water and at a pressure of about 1 atm for a sufficient period of time to cause the amount of cross-linking of the PVP which is desired for that particular implant (see FIG. 1). As an example of this process one might dissolve 75 grams of K-30 PVP and 0.7 grams of sodium bicarbonate in 100 grams of water. A volume of that mixed fluid solution less than that sufficient to fill a thin silicone implant shell is then introduced into such a shell. Next, that solution in the silicone container or shell is treated for a period of 80 hours at 98° C. The filling material will complete its cross-linking in this time at this temperature and will retain its initial weight, volume and shape as a viscous cohesive mass. Thereafter, an amount of water is introduced and the material swells to a size sufficient to fill the shell of interest, and upon sterilization, and possibly neutralization, will be ready for use as an anatomical implant.

Second Embodiment

The previous embodiment of the process requires a mold or container and pre-supposes that the mold or container for the gel-like cohesive mass which will be formed will be implanted as part of the anatomical implant, breast implant or penile implant. This, however, is optional and so is not a necessary characteristic of the process of the invention. The formulation of water, PVP and sodium bicarbonate as mixed can be optionally introduced into a mold other than a mold that will be utilized as a membrane container for the implant. As an example of an alternate mold, one should be able to make a mold of sodium bicarbonate crystals, introduce the fluid and surround the fluid by the sodium bicarbonate mold and then proceed with the process of heating the fluid in the mold at a temperature and pressure less than that required to reach the boiling point of water. This would take approximately 80 hours at a temperature of 98° C. at atmospheric pressure. The desired cohesive mass formed by cross-linking PVP molecules retains almost all of the original water of the formulation. The resulting cohesive mass can then be stabilized in volume and, if desired, neutralized. The mold can be released by physical means, or in the case of sodium bicarbonate, the mold can be dissolved away with water and the insoluble cohesive mass composition could be retrieved. The water solution used to dissolve the sodium bicarbonate would not dissolve the cross-linked PVP and the remaining material retrieved and recovered would be the cohesive mass of insoluble cross-linked PVP in the molded shape that was desired.

It is also anticipated that other ionic molecules such as persulfate or sodium acetate may be used in the initial mixture as an alternative to sodium bicarbonate, but present experiments have involved sodium bicarbonate and sodium hydroxide.

Third Embodiment

In the previous examples, the viscous cohesive mass of water-insoluble, cross-linked PVP material made according to the process when stabilized, and neutralized, maintained its initial volume. In some cases for medical use it is desirable to create a scaffolding of PVP, which maintains its original shape but contains little water. It has been found that a modified sheet form of the viscous cohesive mass of cross-linked insoluble PVP gel-like material of the present invention can be utilized to prevent adhesions after a surgical procedure by placing the sheet between the organs and an incision site (see the Second Embodiment). In addition, in another field of medicine, it would be useful to have a PVP sheet similar to that described, with additional water removed from the sheet to provide a scaffold that would induce and be a suitable scaffold to promote cellular growth either outside or inside the body, in vitro or in vivo.

Accordingly, it is a further aspect of the present invention to provide a procedure that will produce such a sheet structure that is substantially devoid of water. In this case, an appropriate volume of PVP such as K-30 PVP, water, and appropriate weight of sodium bicarbonate, as in the above examples, would be mixed thoroughly and degassed. The fluid mixture would be poured into a container to form a sheet of the desired thickness, which might be approximately one tenth of an inch, or one quarter of an inch, or even one half of a inch thick. The poured mixture would then be heated to 98° C. for approximately 82 hours. At this time a viscous cohesive mass of PVP, insoluble in water, would have formed. The sheet would then be freeze-dried by placing the sheet at a freezing temperature in a vacuum chamber and maintaining those conditions until essentially all the water was removed from the sheet in a well-known manner. Alternatively, substantially all of the water could be removed or driven off from the cohesive mass composition sheet by increasing the temperature (heating in an oven).

Appropriate portions of the freeze-dried sheet in combination with the proper nutrients can be used in vitro or in vivo to grow various mammalian cells. Freeze-drying the cohesive mass in sheet form will maintain and preserve the initial shape of the sheet. If the viscous cohesive mass in sheet form is not freeze-dried, but heat is continued to be applied to the viscous cohesive, insoluble PVP sheet, the trapped water will be driven off and the sheet will become a hard or solid sheet of 20-40 percent of the initial volume of the hydrated gel-like sheet. This method for making solid articles that have more solid properties by driving off the water with vacuum or heat also can be employed when a more solid implant material is desirable.

Fourth Embodiment

For some medical uses it is desirable to have a material such as the PVP described previously injected as filler for tissue. For instance, in the field of urology, the viscous cohesive mass made by the process of the present invention may be used as a bulking material that is introduced to the inside of a sphincter muscle by being injected from a syringe. Such a bulking material is also used for filling tissue in scars, dents of the skin, and for remodeling chins, noses, lips, ears, etc. For this procedure, a formulation of soluble PVP, water and sodium bicarbonate can be introduced into syringes of 1, 2, and 3 cc volumes, for example. The formulated fluid of PVP would be cross-linked inside the syringes. They would be placed in an environment where the syringes could be heated to a temperature less than that of boiling water for a length of time sufficient to enable the desired amount of cross-linking of PVP to occur within the syringe to attain an appropriate viscosity for injection in soft tissues. Thus, if the syringe were heated at 98° C. for a period of 90 hours, for example, a viscosity consistent with that of other materials (injectable bulking materials) would be achieved. This would be a viscosity in excess of 15,000 cp. The reacted material would then be subjected to a stabilizing, and normally a neutralizing, process. Depending on the formulation and conditions under which the cohesive mass is processed and injected, the cohesive cross-linked mass should remain at the site of injection for an indeterminate period, possibly providing permanent or semi-permanent bulking. If small particles of synthetic biocompatible material such as dimethylsiloxane are added to the material, the particles will remain as a permanent bulking agent.

Fifth Embodiment

The object of this novel embodiment is to increase the surface area of the volume of cross-linked PVP material. The first step is to form a substantial volume of the viscous cohesive mass of cross-linked PVP composition such as was described in the Second Process Embodiment. A volume of water is added to the volume of viscous cohesive mass of material in a desired selected ratio, such as 1:1. The cohesive mass, which is insoluble in water, is then mechanically broken into pieces using a vigorous, mechanical disruption means such as a blender, for example. Because each of the small pieces created is hydrophilic on its entire surface, the mixture will become as a fluid that can be used to coat tissue surfaces such as internal organs. In addition to the sheet forms indicated above, such a fluid can be used to coat tissue and organ surfaces during and after surgical procedures to form a barrier that reduces unwanted adhesions between the operative site and internal tissue and organs. This fluid can be administered as a spray or as an injectable depending upon the needs of the surgeon to prevent adhesions.

Sixth Embodiment

This aspect or embodiment of the process of the invention makes use of the higher molecular weight commercial material. The PVP selected is comprised of large molecules, in excess of 100,000 molecular weight. For example, K-60 or K-90 PVP is dissolved in a 0.42% by weight sodium bicarbonate solution and heated at 98° C. for a period of 60 hours to produce a viscous cohesive mass of cross-linked PVP having a viscosity in excess of 15,000 cp up to about 45,000 cp. This hydrophilic material, while highly viscous, can be introduced into a joint using a syringe and needle delivery system. The material is also lubricious and, in this manner, will serve as a lubricant for joint surfaces.

Seventh Embodiment

It is contemplated that the cross-linked PVP material made by the process of the present invention can advantageously be employed for still other medical uses. For example, for some medical uses it would be desirable to have a material such as the cross-linked PVP described in relation to the process of the Second Embodiment, for example, that can be used as a drug delivery system. For instance a drug may advantageously be mixed with a substantial volume of the viscous cohesive mass of cross-linked PVP material such as described in the Second Embodiment. The gel-like material and drug mixture can then be placed in contact with the body as through injection as a bolus, transdermally through contact with the skin or by other well known means. Typically, the drug will migrate out of the cohesive mass and be made available to the body. For example, a PVP viscous cohesive mass was prepared as in the Second Embodiment process and a red, water-soluble, food dye was incorporated into the formulation. The now-colored gel-like insoluble material was placed into a container containing water and allowed to remain in contact with the water. After time, the water became colored red, indicating transfer of dye from the insoluble cohesive mass into the water phase. In another example, a PVP material was prepared using the process of the Second Embodiment and placed into a container containing a water solution of a red, water-soluble, food dye. After time, the bolus of the insoluble composition was removed from the water solution and observed. Quantities of the red dye had migrated into the insoluble cohesive mass. These examples demonstrate that pharmacologically active materials could be delivered to the body via migration into or out of the cohesive mass of cross-linked PVP produced in accordance with the invention. For example, the stabilized gel containing a monoclonal antibody could be placed in a syringe and injected directly into a breast cancer tumor.

The curve of the graphical representation shown in FIG. 1 was derived according to the procedure next described. A water solution comprised of 43% by weight polyvinylpyrrolidone and 0.4% by weight $NaHCO_3$ was heated at 95° C. and a record of the viscosity was measured over a period of 108 hours. A logistic regression was performed on the experimental viscosity over time data. This regression resulted in the following equation:

$$V(t)=A/(1+Be^{ct})+D.$$

Where:
D is a vertical shift to correct for the initial viscosity,
C is an empirically derived growth factor which is affected by temperature and catalyst, and
B and A are constants having to do with the initial viscosity and the final asymptotic viscosity.
"t" is the time variable in which the units are hours and the function V(t) gives the viscosity at time "t" in centipoises.
For this experiment, our values were as follows: A=41254; B=305.09; C=0.074753; D=997.7; e=mathematical constant.
The production of a cross-linked PVP material, which is not soluble in water, per se, is well known and has been reported previously. The procedures reported previously, however, have all involved reacting soluble PVP in a highly alkaline environment and/or employing commercial cross linkers, which formed cross-linked molecules at temperatures in excess of 100° C.

In contrast, all the processes of the present invention involve temperatures less than 100° C. or at least at temperatures and pressures that are low enough to prevent the water in the original formulation from boiling. The process of the invention also allows the insoluble PVP to remain a specific volume and shape and form a cohesive viscous mass of material which has not been possible in previous processes that requires processing temperatures above 100° C. At processing temperatures above 100° C. water is lost and the volume is reduced, therefore the shape and volume is reduced and unpredictable.

The cohesive mass may be produced in a form that can be injected to augment tissue, in addition to a form that can be used as a filling material in anatomical implants. The composition of the present invention may be used in many other applications that require a cohesive gel.

The combination of water-insoluble cohesive gel mixed with PVP soluble in water can be used as an injectable material. Because PVP in the soluble form or in the water-insoluble form is biocompatible and does not illicit a immunological allergenic reaction in the body, the medical devices described previously can be comprised of PVP that has been treated in the manner described to become water-insoluble in the form of a cohesive water-insoluble composition, or the cohesive water-insoluble PVP material can be used in combination with PVP water soluble fluid. A combination of water-soluble and water-insoluble PVP can be used for a biocompatible anti-adhesion composition and in various other medical devices.

Viscosities of the processed cohesive mass material may range from a low of about 10,000 cp to about 45,000 cp or more. A preferred range starts at 15,000 cp or above.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of producing a biocompatible, flexible, elastic cohesive implantable gel comprising:
   (a) thoroughly mixing a volume of water, an amount of polyvinylpyrrolidone (PVP) and an amount of base to form a mixture, said mixture being free of cross-linking agents;
   (b) reacting the mixture at a selected elevated temperature for a sufficient period of time to form a cohesive, water-insoluble gel mass; and
   (c) adding a sufficient volume of water to the cohesive, water-insoluble gel mass of (b) to maximize and stabilize the final volume of the cohesive, water-insoluble gel mass.

2. A method as in claim 1 wherein the base chosen is sodium bicarbonate in an amount by weight of less than 1% of the weight of PVP in the mixture.

3. A method as in claim 2 wherein the mixture is reacted at a temperature of 90° C. to 99° C. until a cohesive water-insoluble gel mass is formed.

4. A method as in claim 1 wherein the base chosen is a metal hydroxide in an amount of from 0.1% to 1.0% of the weight of PVP in the mixture.

5. A method as in claim 4 wherein a temperature treatment of 100° C. or more is chosen for a period of time until a cohesive water-insoluble gel mass is formed.

6. A method as in claim 1 including introducing an amount of the material of (c) into a thin elastomeric implantable container in the general form of a breast and sealing it therein.

7. A method as in claim 1 wherein (a)-(c) are carried out within a thin elastomeric implantable container having the general form of a breast.

8. A method as in claim 1 wherein a therapeutically active material is introduced into the stabilized, cohesive water-insoluble gel mass.

9. A method as in claim 8 wherein the therapeutically active material is comprised of biocompatible particles with a diameter from about 80µ to 500µ.

10. A method as in claim 1 wherein the amount of water (weight) that is absorbed into the reacted cohesive water-insoluble gel mass to stabilize the final volume of the gel mass is up to 30% of the weight of the original PVP water mixture.

11. A method as in claim 1 wherein the polyvinylpyrrolidone (PVP) gel has a viscosity of 15,000 to 45,000 cp.

12. A method as in claim 1 wherein the amount of PVP in the cohesive water-insoluble gel mass is from 33% to 43% of the total weight of the gel mass.

13. A method as in claim 1 including adjusting the pH of the stabilized gel mass to a desired pH by treating the gel mass with an appropriate strength acidic or basic aqueous solution.

14. A method as in claim 13 wherein the basic solution comprises NaOH and the acidic solution comprises HCl.

15. A method as in claim 13 wherein the desired pH is 7.0±0.6.

16. A method as in claim 1 wherein the weight of the amount of PVP is a minimum of about 72% of the weight of the amount of water.

17. A method as in claim 4 wherein the base comprises NaOH.

18. A method of producing a biocompatible, flexible, elastic cohesive implantable gel comprising:
   (a) thoroughly mixing a volume of water, an amount of polyvinylpyrrolidone (PVP) and an amount of base;
   (b) reacting the mixture at a selected elevated temperature for a sufficient period of time to form a cohesive, water-insoluble gel mass; and
   (c) adding a sufficient volume of water to the cohesive, water-insoluble gel mass of (b) to maximize and stabilize the final volume of the cohesive, water-insoluble gel mass wherein the base chosen is sodium bicarbonate in an amount by weight of less than 1% of the weight of PVP in the mixture.

19. A method as in claim 18 wherein the mixture is reacted at a temperature of 90° C. to 99° C. until a cohesive water-insoluble gel mass is formed.

* * * * *